(12) United States Patent
Jallon

(10) Patent No.: US 9,445,752 B2
(45) Date of Patent: Sep. 20, 2016

(54) SYSTEM AND METHOD FOR DETERMINING THE POSTURE OF A PERSON

(75) Inventor: Pierre Jallon, Grenoble (FR)

(73) Assignees: Commissariat A L'energie Atomique et Aux Energies Alternatives, Paris (FR); Movea, Grenoble (FR)

( * ) Notice: Subject to any disclaimer, the term of this patent is extended or adjusted under 35 U.S.C. 154(b) by 210 days.

(21) Appl. No.: 13/264,965

(22) PCT Filed: Apr. 26, 2010

(86) PCT No.: PCT/EP2010/055562
§ 371 (c)(1),
(2), (4) Date: Feb. 23, 2012

(87) PCT Pub. No.: WO2010/122174
PCT Pub. Date: Oct. 28, 2010

(65) Prior Publication Data
US 2012/0143094 A1    Jun. 7, 2012

(30) Foreign Application Priority Data

Apr. 24, 2009  (FR) .................................... 09 52694

(51) Int. Cl.
*A61B 5/11*    (2006.01)
*A61B 5/00*    (2006.01)
*G06K 9/00*    (2006.01)

(52) U.S. Cl.
CPC ............ *A61B 5/1116* (2013.01); *A61B 5/1118* (2013.01); *A61B 5/1123* (2013.01); *A61B 5/4094* (2013.01); *G06K 9/00335* (2013.01)

(58) Field of Classification Search
CPC ..................................................... A61B 5/1116
USPC ........................................ 600/595; 340/573.7
See application file for complete search history.

(56) References Cited

U.S. PATENT DOCUMENTS

| | | | |
|---|---|---|---|
| 8,152,694 B2 * | 4/2012 | Srinivasan et al. | ........... 600/595 |
| 2007/0175406 A1 | 8/2007 | Liang et al. | |
| 2008/0275349 A1 | 11/2008 | Halperin et al. | |

FOREIGN PATENT DOCUMENTS

EP    1 731 097 A    12/2006

OTHER PUBLICATIONS

Foerster et al., Detection of posture and motion by accelerometry: a validation study in ambulatory monitoring, 1997, Computers in Human Behavior, vol. 15, pp. 571-583.*

(Continued)

*Primary Examiner* — Linda Dvorak
*Assistant Examiner* — Emily Lloyd
(74) *Attorney, Agent, or Firm* — Stroock & Stroock & Lavan LLP

(57) ABSTRACT

A system for determining the posture of a person has a motion sensor (CM) with at least one axis of measurement, which is provided with fixing means (MF) for rigidly connecting said motion sensor (CM) to a user. Analysis means (AN) are also included for determining a posture of the user. The analysis means (AN) utilize: (A) joint densities of probabilities of a low-frequency component and a high-frequency component, these densities of probabilities being defined for each posture; and (B) probabilities of transition between two successive postures.

12 Claims, 3 Drawing Sheets

(56) References Cited

OTHER PUBLICATIONS

Lehmann, Kevin, "Gaussian Distributions", 1997, Princeton University, pp. 1-25.*

Teotia, Seemant, "Appendix B—The Chi-Square Distribution" of Saddlepoint Approximation for Calculating Performance Spectrum-Sliced WDM Systems (available at http://vtechworks.lib.vt.edu/handle/10919/34329), 1999, VTechWorks, pp. 92-100.*

Jeff A. Bilmes: "A Gentle Tutorial of the EM Algorithm and its Application to Parameter Estimation for Gaussian Mixture and . . . ", Int' Computer Science Institute, Apr. 1998.

Jallon P et al: "Detection system of motor epileptic seizures through motion analysis with 3D accelerometers" Engineering in Medicine and Biology Society, Sep. 2009.

International Search Report and Written Opinion dated Aug. 10, 2010, issued in counterpart International Application No. PCT/EP2010/05562.

* cited by examiner

SYSTEM AND METHOD FOR DETERMINING THE POSTURE OF A PERSON

CROSS-REFERENCE TO RELATED APPLICATIONS

This application is a national phase application under §371 of PCT/EP2010/055562, filed Apr. 26, 2010, which claims priority to French Patent Application No. 0952694, filed Apr. 24, 2009, both of which are incorporated herein by reference in their entirety.

BACKGROUND OF THE INVENTION

1. Field of the Invention

The present invention relates to a system and a method for determining the posture of a person.

2. Description of the Related Art

Systems and methods are known which relate to the analysis of movement on the basis of a hidden Markov model, as described, for example, in the documents entitled "Gesture recognition using the XWand" by Daniel Wilson and Andy Wilson and "Motion-based gesture recognition with an accelerometer" (bachelor's thesis) by P. V. Borza.

The document entitled "A hidden Markov model-based stride segmentation technique applied to equine inertial sensor trunk movement data", Journal of Biomechanics 41 (2008) 216-220, by Thilo Pfau, Marta Ferrari, Kevin Parsons, and Alan Wilson, relates to the analysis of a horse's gait.

However, these systems and methods have a limited accuracy.

BRIEF SUMMARY OF THE INVENTION

One object of the invention is to improve the accuracy of the determination of the activity of a mobile element, particularly for a living being, either human or animal.

According to one aspect of the invention, a system is disclosed for determining the posture of a person, comprising at least two signal processing pathways at the output of at least one motion sensor (CM) substantially affixed to said person, wherein one of the at least two processing pathways processes first signals with frequencies higher than a first threshold (S1), the other processing pathway processing second signals with frequencies below a second threshold (S2) lower than or equal to said first threshold (S1), said system further comprising:

calculation means (CALC) for calculating a density of probability ($P_y$) of a first variable representing said first signals (HF) defined by a Chi-2 law with a degree of freedom equal to a number of measurement axes (k) taken into account from the at least one motion sensor (CM), and a density of probability ($P_x$) of a second variable representing said second signals (BF) defined by a Gaussian law; and analysis means (AN) suitable for determining a posture of the user, these analysis means (AN) combining:

joint densities of probabilities of said first and second variables, these densities of probabilities being defined for each posture; and probabilities of transition between two successive postures.

It is noted that a hidden Markov model may be defined by two random processes: a first which is referred to as a "state" in embodiments of the present application and which is not observed, or, in other words, which is hidden, and a second, which is the observation of that the density of probability at a given time depends on the value of the state at the same time. According to this first aspect of the invention, the state assumes discrete values.

A system of this type allows the activity of a mobile element to be determined, particularly for a living being, either human or animal, with improved accuracy.

In one embodiment, said determination means are suitable for determining a one-dimensional low-frequency component equal to a linear combination of the measures according to the axes of measurement taken into account by the movement sensor, said high-frequency component being defined by a Chi-2 law with a degree of freedom.

According to one embodiment, the density of probability of a pair of values for the low-frequency component and the high-frequency component includes the product of a density of probability of obtaining the value for the low-frequency component and the density of probability of obtaining the value for the high-frequency component, said densities of probability being defined, for each state i, by the following expressions:

$$\begin{cases} P_{x,i}(x(n)) = \dfrac{1}{\sqrt{2\pi}\,\sigma_{xi}} \cdot e^{-\dfrac{(x(n)-\mu_{x,i})^2}{2\sigma_{x,i}^2}} \\ p_{y,i}(y(n)) = \dfrac{1}{\sqrt{2^k}\,\sigma_{y,i}^k \Gamma\!\left(\dfrac{k}{2}\right)} y(n)^{k/2-1} e^{-\dfrac{y(n)}{2\sigma_{y,i}^2}} \end{cases}$$

where:

x(n) is a signal of dimension 1, representing the low-frequency component with the index sample n;

$\mu_{x,i}$ represents a vector of the same dimension as the low-frequency component, representing the state i of the hidden Markov model concerned;

$\sigma_{x,i}$ represents the square root of the variance of the low-frequency component x, representing the state of the hidden Markov model i concerned;

y(n) represents the high-frequency component with the index sample n;

k represents the number of axes of measurement taken into account by the movement sensor;

$\sigma_{y,i}$ is a quantity proportional to the temporal mean of the variable y(n) in the state i. For example, $\sigma_{y,i}$ is the temporal mean of the variable y(n) divided by k, and Γ is the gamma function verifying $\Gamma(\tfrac{1}{2})=\sqrt{\pi}$, $\Gamma(1)=1$ and $\Gamma(n+1+\tfrac{1}{2})=n\delta(n+\tfrac{1}{2})$.

A modeling of this type of the observed signals is suitable for the majority of possible cases.

In one embodiment, the system includes display means.

According to one embodiment, said movement sensor includes an accelerometer and/or a magnetometer and/or a gyrometer.

In one embodiment, the system includes a first accelerometer with an axis of measurement and fixing means suitable for fixing the first accelerometer to the torso of the user in such a way that the axis of measurement coincides with the vertical axis VT of the body when the user is upright.

According to one embodiment, said analysis means are suitable for determining a posture of the user as a function of time, by using a hidden Markov model with a maximum of four states from the standing or seated posture, the walking posture, the leaning posture and the recumbent posture.

The hidden Markov model can then be defined by:
an unobserved discrete process, denoted the state, which assumes four values from the following: the standing or seated posture, the walking posture, the leaning posture and the recumbent posture. This variable or state can be a Markov sequence of order 1, and is therefore characterized by the probabilities of transition from one state to another; and the observed process of the hidden Markov model is the multidimensional signal (x(n), y(n)), of which the density of probability depends on the state (the hidden process) at a given time. This density of probability corresponds to the joint density of probability previously defined by the following relation:

$$P(x(n),y(n)|\text{State}=i) = P_{iState}(x(n),y(n)) = P_{x,i}(x(n)) P_{y,i}(y(n))$$

Examples of parameters of the densities of probabilities $P_{x,i}$ and $P_{y,i}$ as a function of the different states, or postures, can be found below. The words 'state' and 'posture' are synonymous throughout this application. In a specific embodiment:
for the standing or seated posture, $\mu_x \in [0.7; 1.3]$, $\sigma_x \in [0.05; 0.4]$, $\sigma_y \in [1.10^{-3}; 5.10^{-1}]$;
for the walking posture, $\mu_x \in [0.7; 1.3]$, $\sigma_x \in [0.05; 0.4]$, $\sigma_y \in [1.10^{-2}; 1]$;
for the leaning posture, $\mu_x \in [0.7; 1.3]$, $\sigma_x \in [0.05; 0.4]$, $\sigma_y \in [1.10^{-3}; 5.10^{-1}]$; and
for the recumbent posture $\mu_x \in [-0.3; 0.3]$, $\sigma_x \in [0.05; 0.4]$, $\sigma_y \in [1.10^{-3}; 5.10^{-1}]$.

$P_i(x(n),y(n))$ represents the density of probability associated with the state i, at the time n, of x(n) and y(n). It corresponds to the product of the densities of probabilities $P_{x,i}(x(n))$ and $P_{y,i}(y(n))$ previously defined. If a quantity $\theta(n)$ is considered, combining the observed data x(n) and y(n), it can be written that $P_i(x(n),y(n))=P_i(\theta(n))=p(\theta(n)/E(n)=i)$, where E(n) represents the state at the time n. $\theta(n)=\{x(n), y(n)\}$.

However, the determination of the state E(n) at the time n purely on the basis of the observed data y(n) and the associated densities of probabilities $P_{y,i}(y(n))$ is generally not satisfactory. In fact, the observation of a single sample does not generally allow an attitude to be determined: a plurality of samples are preferably observed.

Thus, if E(0:N) denotes the sequence of states between the time n=0 and the time n=N, and if $\theta(0:N)$ denotes the data observed between the time n=0 and the time n=N, the probability of the sequence of states E(0:N) corresponding to the sequence of states E(0), E(1) . . . E(N) is written as $p(E(0:N)|\theta(0:N-1))$, which is proportional to:

$$p(E(0))p(\theta(0)/E(0))\prod_{n=1}^{N} p(E(n)/E(n-1))p(\theta(n)/E(n))$$

For example, for the sequence E(0:N)={i, i, i, . . . , i}, this probability is written as follows:

$$p(E(0)=i)p(\theta(0)|E(0)=i))\prod_{n=1}^{N} p(E(n)=i|E(n-1)=i)) \quad (1)$$
$$p(\theta(n)|E(n)=i))$$

The estimated sequence of states E(0:N) is the sequence with the highest probability. In practice, rather than considering all of the possible sequences and calculating the probability for each one, a Viterbi algorithm can advantageously be used to estimate this sequence.

P(E(0)) denotes the probability associated with the initial state E(0). For example, an equiprobable distribution of each of the possible states can be chosen if n=0.

$p(\theta(0)/E(0))$ represents the probability of observation of the data $\theta(0)$ at the time E(0). This corresponds to the probability $P_i(x(n=0),y(n=0))$ where E(n)=i.

$p(E(n)/E(n-1))$ represents the probability of being in a state E(n) at the time of being in a state E(n-1) at the time n-1.

$p(\theta(n)/E(n))$ represents the probability of observing the quantities $\theta(n)$ when in the state E(n). This corresponds to the probability $P_i(x(n),y(n))$ with E(n)=i.

In one embodiment, the system further includes a second accelerometer with an axis of measurement and fixing means suitable for fixing the second accelerometer to the thigh of the user in such a way that the axis of measurement coincides with the vertical axis VT of the body when the user is upright.

For example, said analysis means are suitable for determining a posture of the user as a function of time, by using a hidden Markov model with a maximum of four states from the standing posture, the seated posture, the recumbent posture and the walking posture.

A system of this type allows the posture of a person to be calculated in real time.

According to one embodiment, x(n) represents the pair of respective low-frequency components of said two accelerometers, and y(n) represents the high-frequency component of said second accelerometer, with the index sample n, the density of probability of obtaining the value x(n) corresponding to the state i being defined by the following expression:

$$P_{x,i}(x(n)) = \frac{1}{\sqrt{(2\pi)^2|\Sigma_{x,i}|}} \cdot e^{-\frac{1}{2}(x(n)-\mu_{x,i})^T \Sigma_{x,ii}^{-1}(x(n)-\mu_{x,i})}$$

where:
$\Sigma_{x,i}$ is a diagonal matrix of dimension 2 describing the covariance matrix of the signal x(n) for the state i of the model.
$\mu_{x,i}$ represents a two-component column vector, representing the state i of the model.

The probabilities of the variables x(n) and y(n) associated with these states are defined by the above probabilities, with the following parameters:
for the standing posture (state 1), the parameters of the densities of probability can be defined as follows: $\mu_{x,1}=[1\ 1]^T$ and $$\Sigma_{x,1} = \begin{bmatrix} 0.03^2 & 0 \\ 0 & 0.03^2 \end{bmatrix}$$

For the high-frequency component y(n), its parameter can be as follows: $\sigma_{y,1}=3e^{-2}$;
for the seated posture (state 2), the parameters of the densities of probability can be defined as follows: $\mu_{x,2}=[1\ 0]^T$ and $$\sum\nolimits_{x,2} = \begin{bmatrix} 0.03^2 & 0 \\ 0 & 0.03^2 \end{bmatrix}.$$

For the high-frequency component y(n), its parameter can be as follows: $\sigma_{y,2}=3e^{-2}$;

for the recumbent posture (state 3), the parameters of the densities of probability can be defined as follows: $\mu_{x,3}=[0\ 0]^T$ and $$\sum\nolimits_{x,3} = \begin{bmatrix} 0.03^2 & 0 \\ 0 & 0.03^2 \end{bmatrix}.$$

For the high-frequency component y(n), its parameter can be as follows: $\sigma_{y,3}=3e^2$;

for the walking posture (state 4), the parameters of the densities of probability can be defined as follows: $\mu_{x,4}=[1\ 1]^T$ and $$\sum\nolimits_{x,4} = \begin{bmatrix} 0.03^2 & 0 \\ 0 & 0.03^2 \end{bmatrix}.$$

For the high-frequency component y(n), its parameter can be as follows: $\sigma_{y,4}=1.2e^{-1}$;

Thus, according to the reasoning detailed above, if E(0:N) denotes the sequence of states between the time n=0 and the time n=N, and if θ(0:N) denotes the data observed between the time n=0 and the time E(0,N) corresponds to the sequence of states E(0), E(1) . . . E(N) maximizing the expression:

$$p(E(0))p(\theta)(0)/(0))\prod_{n=1}^{N} p(E(n)/E(n-1))p(\theta(n)/E(n)) \quad (1)$$

According to this embodiment, θ(n)={x(n), y(n)}, x(n) and y(n) respectively being said low and high-frequency components of the signal S(n) measured by two accelerometers at the time n.

According to a different aspect of the invention, a method is disclosed for determining the posture of a person, wherein:

at least two processing pathways are configured at the output of a motion sensor (CM), the first pathway processing first signals with frequencies above a first threshold (S1), and the second pathway processing second signals with frequencies below a second threshold (S2) lower than or equal to said first threshold (S1);

a density of probability ($P_y$) of a first variable representative of said first signals (HF) and a density of probability ($P_x$) of a second variable representative of said second signals (BF) are calculated, said first variable being defined by a Chi-2 law with a degree of freedom equal to the number of axes of measurement taken into account (k) from the motion sensor (CM), and said second variable being defined by a Gaussian law; and a posture of the person is determined as a function of time, by using a hidden Markov model with N states corresponding respectively to N postures, this determination being carried out by combining:

joint densities of probabilities of said second and first variables, these densities of probabilities being defined for each posture, and probabilities of transition between two successive postures.

BRIEF DESCRIPTION OF THE DRAWINGS

The invention will be better understood by studying a number of embodiments described as non-limiting examples and illustrated by the attached drawings, in which.

DETAILED DESCRIPTION

Figure 1A:
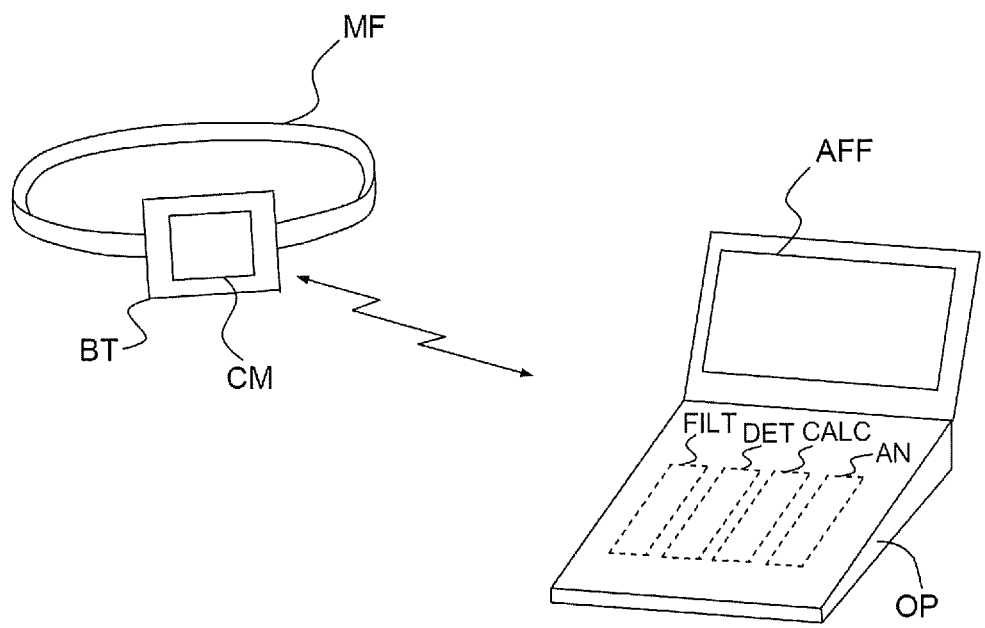
FIG. 1 shows a system according to one aspect of the invention.

FIG. 1 shows an embodiment system for determining the posture of a person, including at least one motion sensor CM with at least one axis of measurement, disposed in a housing BT, provided with fixing means including, for example, an elastic element, for rigidly connecting the movement sensor CM to a user. The motion sensor CM may be an accelerometer, a magnetometer or a gyrometer, with one, two or three axes of measurement.

The system includes a filter FILT to select, for each axis of measurement of the motion sensor CM, high frequencies above a first threshold S1, and low frequencies below a second threshold S2 lower than or equal to the first threshold S1. The system also includes a determination module DET for determining a one-dimensional high-frequency component HF equal to the sum of the squares of said high frequencies of the axes of measurement taken into account by the motion sensor CM, and a one-dimensional low-frequency component BF equal to a linear combination of the measurements according to axes of measurement taken into account by the motion sensor CM.

The system also includes a calculation module CALC for calculating the square of the variance of the probability $P_y$ of said high-frequency component HE and the square of the variance of the probability $P_x$ of said low-frequency component BF, said high-frequency component HF being defined by a Chi-2 law with a degree of freedom, and said low-frequency component BF being defined by a Gaussian law.

Analysis means AN allow a posture of the user to be determined as a function of time, by using a hidden Markov model with N states corresponding respectively to N postures.

For each state i, the density of probability of joint probability $P_i(x(n),y(n))$ of obtaining a pair of values (x(n), y(n)) for the low-frequency component BF and the high-frequency component HF being equal to the product of the density of probability $P_{x,i}$ of obtaining the value x(n) for the low-frequency component BF and the density of probability $P_{y,i}$ of obtaining the value y(n) for the high-frequency component HF, the densities of probability $P_{x,i}$, $P_{y,i}$ are defined for each state i by the following expressions:

$$\begin{cases} P_{x,i}(x(n)) = \dfrac{1}{\sqrt{2\pi}\,\sigma_{x,i}} \cdot e^{-\dfrac{(x(n)-\mu_{x,i})^2}{2\sigma_{x,i}^2}} \\ p_{y,i}(y(n)) = \dfrac{1}{\sqrt{2^k}\,\sigma_{y,i}^k \Gamma\left(\dfrac{k}{2}\right)} y(n)^{k/2-1} e^{-\dfrac{y(n)}{2\sigma_{y,i}^2}} \end{cases}$$

where:

x(n) represents the low-frequency component with the index sample n;

$\mu_{x,i}$ represents a vector with the same dimension as the low-frequency component, representing the state i of the hidden Markov model concerned;

$\sigma_{x,i}$ represents the square root of the variance of the low-frequency component x, representing the state of the hidden Markov model i concerned;

y(n) represents the high-frequency component with the index sample n;

k represents the number of axes of measurement taken into account by the movement sensor;

$\sigma_{y,i}$ is a quantity proportional to the temporal mean of the variable y(n), in the state i. For example, $\sigma_{y,i}$ is the temporal mean of the variable y(n) divided by k; and $\Gamma$ is the gamma function verifying $\Gamma(\frac{1}{2})=\sqrt{\pi}$, $\Gamma(1)=1$ and $\Gamma(n+1+\frac{1}{2})=n\Gamma(n+\frac{1}{2})$.

The system also includes a display screen AFF.

In a first example, the system includes an accelerometer with an axis of measurement and a fixing element for fixing the accelerometer to the torso of the user in such a way that the axis of measurement coincides with the vertical axis VT of the body when the user is upright.

The hidden Markov model used includes four states corresponding to four postures, the standing or seated posture (state 1), the walking posture (stage 2), the leaning posture (state 3), and the recumbent posture (state 4). The states of the hidden Markov model are defined as follows:

the standing or seated posture (state 1): $\mu_{x,1}=1$, $\sigma_{x,1}=0.2$, and $\sigma_y=3e^{-2}$;

the walking posture (state 2): $\mu_x=1$, $\sigma_{x,2}=0.2$, and $\sigma_y=1.2e^{-1}$;

the leaning posture (state 3): $\mu_x=0.5$, $\sigma_{x,3}=0.2$, and $\sigma_y=3e^{-2}$;

the recumbent posture (state 4): $\mu_x=0$, $\sigma_{x,4}=0.2$, and $\sigma_y=3e^{-2}$.

At each time n, a state of the person can then be determined as follows:

$$E(n)=\arg_i \max(P_{x,i}(x(n))P_{y,i}(y(n))=\arg_i \max(P_i(x(n),y(n))$$

If, at the time n, the person is in the state i, E(n)=i.

$P_i(x(n),y(n))$ represents the density of probability associated with the state i, at the time n, of x(n) and y(n). It corresponds to the product of the densities of probabilities $P_{x,i}(x(n))$ and $P_{y,i}(y(n))$ previously defined. If a quantity $\theta(n)$ is considered, combining the observed data x(n) and y(n), it can be written that $P_i(x(n),y(n))=P_i(\theta(n))=p(\theta(n)/E(n)=i)$, where E(n) represents the state at time n.

However, the determination of the state E(n) at the time n purely on the basis of the observed data x(n) and y(n) and the associated densities of probabilities $P_{x,i}(x(n))$ and $P_{y,i}(y(n))$, respectively associated with these data is generally not satisfactory.

Experience shows that it is desirable to take into account an a priori, and, for example, the state E(n−1) determined during the time n−1.

Thus, if E(0:N) denotes the sequence of states between the time n=0 and the time n=N, and if $\theta$(0:N) denotes the data observed between the time n=0 and the time n=N, the probability of the sequence of states E(0:N) corresponding to the sequence of states E(0), E(1) . . . E(N) is written as p(E(0:N)|θ(0:N−1)), which is proportional to:

$$p(E(0))p(\theta(0)/E(0))\prod_{n=1}^{N} p(E(n)/E(n-1))p(\theta(n)/E(n))$$

For example, for the sequence E(0:N)={i, i, i, . . . , i}, this probability is written as follows:

$$p(E(0) = i)p(\theta(0) | E(0) = i))\prod_{n=1}^{N} p(E(n) = i | E(n-1) = i)) \quad (1)$$

$$p(\theta(n) | E(n) = i))$$

The estimated sequence of states E(0:N) is the sequence with the highest probability. In practice, rather than considering all of the possible sequences and calculating the probability for each one, a Viterbi algorithm can advantageously be used to estimate this sequence.

P(E(0)) denotes the probability associated with the initial state E(0). For example, an equiprobable distribution of each of the possible states can be chosen if n=0.

p(θ(0)/E(0)) represents the probability of observation of the data θ(0) at time E(0). This corresponds to the probability $P_i(x(n=0),y(n=0))$ where E(n)=i.

p(E(n)/E(n−1)) represents the probability of being in a state E(n) when a state E(n−1) prevailed at the time n−1.

p(θ(n)/E(n)) represents the probability of observing the quantities θ(n) when in the state E(n). This corresponds to the probability $P_i(x(n),y(n))$ with E(n)=i.

The probabilities p(E(n)/E(n−1)) correspond to probabilities of transition from a state E(n−1) to a state E(n). These probabilities are indicated in the following table by adopting the notations E(n−1)=j and E(n)=i.

The sequence of states E(0) . . . E(N) maximizing the expression (1) can be obtained, for example, by using the Viterbi algorithm, which is well known to the person skilled in the art.

Thus, 1) by establishing, for each state E(n):
   the probability of observing the quantities θ(n) in the state E(n), denoted p(θ(n)/E(n))
   the probability of transition from a state E(n−1) to a state E(n), denoted p(E(n)/E(n−1))
2) by establishing the probability associated with each state E(0),
3) by obtaining the values observed θ(n) at each time n between n=0 and n=N, the most probable sequence of states E(0) . . . E(N) can be obtained.

It is noted that, in the present description, θ(n)={x(n), y(n)}, where x(n) and y(n) are respectively said low and high-frequency components of the signal S(n) measured by an accelerometer at the time n.

The densities of probabilities of transition $P(state_i/state_j)$ from a state $state_i$ corresponding to a posture of the hidden Markov model to a different state $state_j$ corresponding to a posture of the hidden Markov model can be as follows, chosen in such a way as to provide the system with good stability:

| P(state$_i$/state$_j$) | state$_i$ = 1 (standing or seated) | state$_i$ = 2 (walking) | state$_i$ = 3 (leaning) | state$_i$ = 4 (recumbent) |
|---|---|---|---|---|
| state$_i$ = 1 (standing or seated) | 0.8 | 0.1 | 0 | 0.1 |
| state$_i$ = 2 (walking) | 0.1 | 0.8 | 0.1 | 0 |
| state$_i$ = 3 (leaning) | 0.1 | 0.1 | 0.8 | 0 |
| state$_i$ = 4 (recumbent) | 0.1 | 0 | 0 | 0.9 |

On the basis of the input signals and the hidden Markov model as defined, the analysis module AN determines the most probable sequence of states (postures) according to conventional procedures, for example by calculating the associated probability for all of the possible sequences of states, taking into account the observed signal and keeping the most probable sequence, as described, for example, in the document entitled "An introduction to hidden Markov models" by L. R. Rabiner and B. H. Juang, IEEE ASSP Magazine, January 1986, or in the book entitled "Inference in Hidden Markov Models" by Cappé, Moulines and Ryden from Springer, from the series entitled "Springer series in statistics".

Figure 1B:
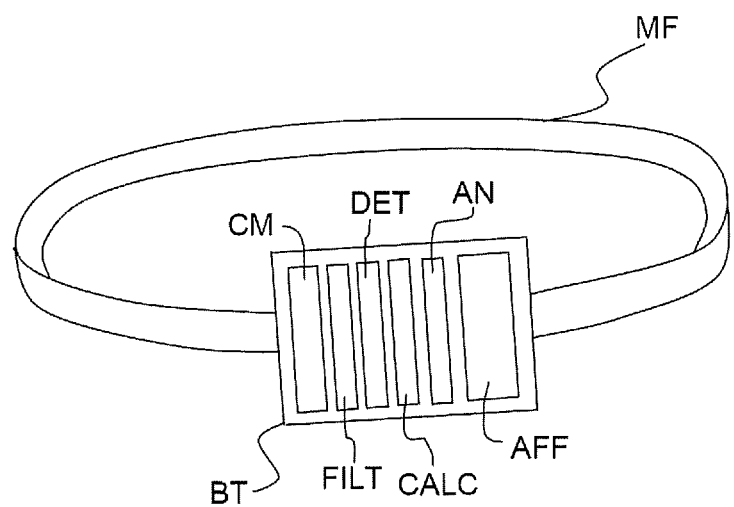

The different elements of the system may, for example, be integrated into the same housing BT, as shown in FIG. 1a, or some elements may be located externally, for example on a portable computer OP, as shown in FIG. 1b.

Figure 2:
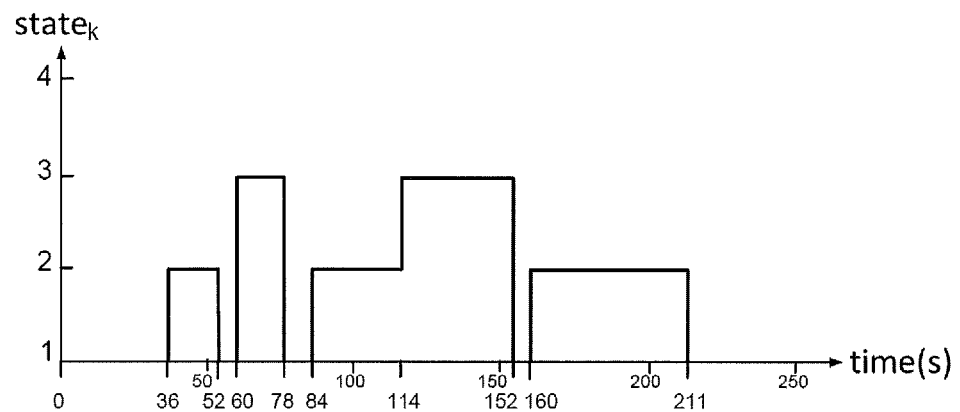
FIG. 2 shows an example of a recording of a system according to one aspect of the invention.
Figure 2:
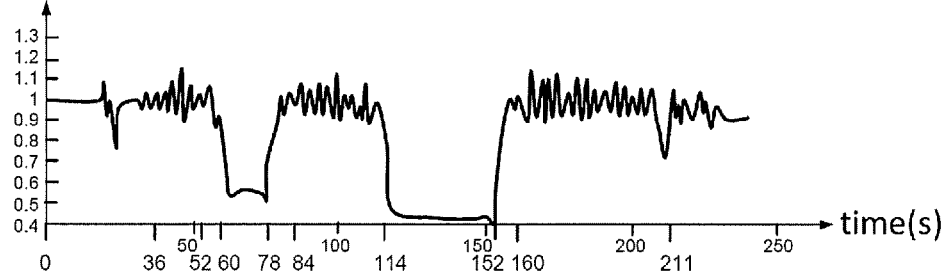

FIG. 2 shows an example of a recording of a user of the system in the first example, in the lower graph, and the result supplied by the system which indicates that the user has been in the standing or seated posture (state 1) for 36 seconds, then in the walking posture (state 2) for 16 seconds, then in the standing or seated posture (state 1) for 8 seconds, then in the leaning posture (state 3) for 18 seconds, then in the standing or seated posture (state 1) for 6 seconds, then in the walking posture (state 2) for 30 seconds, then in the leaning posture (state 3) for 38 seconds, then in the standing or seated posture (state 1) for 8 seconds, then in the walking posture (state 2) for 51 seconds, and finally finishes in the standing or sitting posture (state 1).

In a second example, the system includes a first accelerometer with an axis of measurement and a first fixing element to fix the first accelerometer to the torso of the user in such a way that the axis of measurement coincides with the vertical axis VT of the body when the user is upright, and a second accelerometer with an axis of measurement and a second fixing element to fix the second accelerometer to the thigh of the user in such a way that the axis of measurement coincides with the vertical axis VT of the body when the user is upright.

The hidden Markov model used includes four states corresponding to four postures, the standing posture (state 1), the seated posture (state 2), the recumbent posture (state 3), and the walking posture (state 4).

In this case, x(n) represents the pair of respective low-frequency components BF of said two accelerometers, and y(n) represents the high-frequency component HF of said second accelerometer, with the index sample n, the density of probability $P_x$ of obtaining the value x(n) being defined by the following expression:

$$P_{x,i}(x(n)) = \frac{1}{\sqrt{(2\pi)^2|\Sigma_{x,i}|}} \cdot e^{-\frac{1}{2}(x(n)-\mu_{x,i})^T \Sigma_{x,i}^{-1}(x(n)-\mu_{x,i})}$$

where:

$\Sigma_{x,i}$ is a diagonal matrix of dimension 2 describing the covariance matrix of the signal x(n) for the state i of the model.

$\mu_{x,i}$ represents a two-component column vector, representing the state i of the model.

The probabilities of the variables x(n) and y(n) associated with these states are defined by the above probabilities, with the following parameters:

for the standing posture (state 1), the parameters of the densities of probability can be defined as follows: $\mu_{x,1}=[1\ 1]^T$ and $$\sum\nolimits_{x,1} = \begin{bmatrix} 0.03^2 & 0 \\ 0 & 0.03^2 \end{bmatrix}.$$

For the high-frequency component y(n), its parameter can be as follows: $\sigma_{y,1}=3e^{-2}$;

for the seated posture (state 2), the parameters of the densities of probability can be defined as follows: $\mu_{x,2}=[1\ 0]^T$ and $$\sum\nolimits_{x,2} = \begin{bmatrix} 0.03^2 & 0 \\ 0 & 0.03^2 \end{bmatrix}.$$

For the high-frequency component y(n), its parameter can be as follows: $\sigma_{y,2}=3e^{-2}$;

for the recumbent posture (state 3), the parameters of the densities of probability can be defined as follows: $\mu_{x,3}=[0\ 0]^T$ and $$\sum\nolimits_{x,3} = \begin{bmatrix} 0.03^2 & 0 \\ 0 & 0.03^2 \end{bmatrix}.$$

For the high-frequency component y(n), its parameter can be as follows: $\sigma_{y,3}=3e^{-2}$;

for the walking posture (state 4), the parameters of the densities of probability can be defined as follows: $\mu_{x,4}=[1\ 1]^T$ and $$\sum\nolimits_{x,4} = \begin{bmatrix} 0.03^2 & 0 \\ 0 & 0.03^2 \end{bmatrix}.$$

For the high-frequency component y(n), its parameter can be as follows: $\sigma_{y,4}=1,2e^{-1}$;

Thus, according to the embodiment reasoning detailed above, if, E(0:N) denotes the sequence of states between the time n=0 and the time n=N, and if θ(0:N) denotes the data observed between the time n=0 and the time n=N, E(0,N) corresponds to the sequence of states E(0), E(1) . . . E(N) maximizing the expression:

$$p(E(0))p(\theta(0)/E(0))\prod_{n=1}^{N} p(E(n)/E(n-1))p(\theta(n)/E(n)) \quad (1)$$

According to this embodiment, $\theta(n)=\{x(n), y(n)\}$, where $x(n)$ and $y(n)$ are respectively said low-frequency and high-frequency components of the signal $S(n)$ measured by two accelerometers at the time n.

The densities of probabilities of transition $P(state_i/state_j)$ from a state $state_i$ corresponding to a posture of the hidden Markov model to a different state $state_j$ corresponding to a posture of the hidden Markov model can be as follows, chosen in such a way as to provide the system with good stability:

| $P(state_i/state_j)$ | $state_i = 1$ standing | $state_i = 2$ (seated) | $state_i = 3$ (recumbent) | $state_i = 4$ (walking) |
|---|---|---|---|---|
| $state_j = 1$ standing | 0.8 | 0.1 | 0 | 0.1 |
| $state_j = 2$ (seated) | 0.1 | 0.8 | 0.1 | 0 |
| $state_j = 3$ (recumbent) | 0.1 | 0.1 | 0.8 | 0 |
| $state_j = 4$ (walking) | 0.1 | 0 | 0 | 0.9 |

On the basis of the input signals and the hidden Markov model as defined, the analysis module AN determines the most probable sequence of states (postures) according to conventional procedures, for example by calculating the associated probability for all of the possible sequences of states, taking into account the observed signal and keeping the most probable sequence, as described, for example, in the document entitled "An introduction to hidden Markov models" by L. R. Rabiner and B. H. Juang, IEEE ASSP Magazine, January 1986, or in the book entitled "Inference in Hidden Markov Models" by Cappé, Moulines and Ryden from Springer, from the series entitled "Springer series in statistics".

Figure 3:
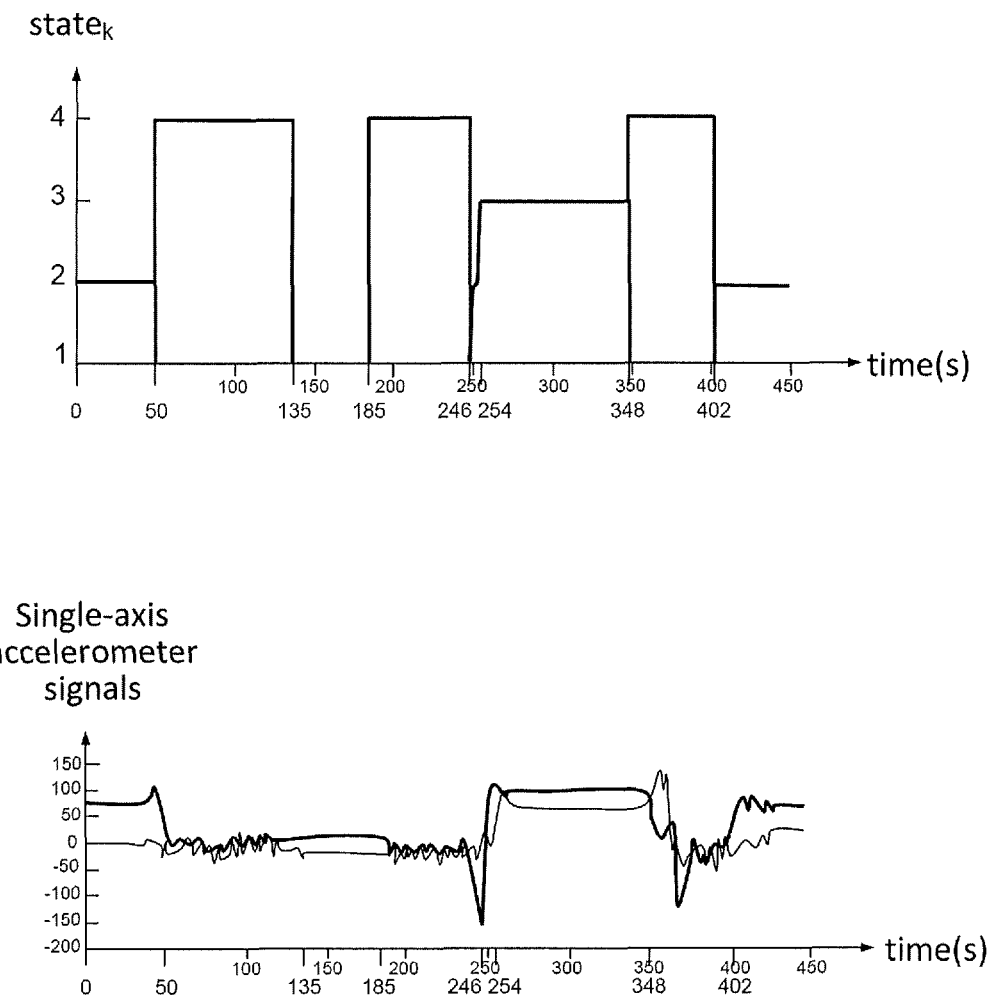
FIG. 3 shows an example of a recording of a system according to a different aspect of the invention.

FIG. 3 shows an example of a recording of a user of the system shown in the first example, in the lower graph, and the result supplied by the system which indicates that the user has been in the seated posture (state 2) for 50 seconds, then in the walking posture (state 4) for 85 seconds, then in the standing posture (state 1) for 50 seconds, then in the walking posture (state 4) for 61 seconds, then in the seated posture (state 2) for 8 seconds, then in the recumbent posture (state 3) for 94 seconds, then in the walking posture (state 4) for 54 seconds, and finally finishes in the seated posture (state 2).

Embodiments of the present invention enable the posture of a person to be determined, in real time or deferred, at reduced cost and with improved accuracy, by accurately determining the changes of posture.

The invention claimed is:

1. A system for determining a posture of a person, comprising:
    at least one motion sensor configured to be affixed to the person, the at least one motion sensor configured to measure k measurement axes, k being greater than or equal to two;
    at least one filter coupled to the at least one motion sensor and configured to generate output signals that include first signals with frequencies higher than a first threshold selected for each axis of measurement, and second signals with frequencies below a second threshold lower than or equal to said first threshold;
    a calculation module configured to calculate a density of probability of a first variable representing said first signals, said first variable modeled by a Chi-2 law with a degree of freedom equal to k, and to calculate a density of probability of a second variable representing said second signals, said second variable being a one-dimensional variable representative of the second signals along the k axes of measurement and being modeled by a Gaussian law; and
    an analysis module configured to determine a posture of the person out of a plurality of postures by combining:
        joint densities of probabilities of said first and second variables, the joint densities of probabilities being defined for each posture of the plurality of postures; and
        probabilities of transition between two successive postures of the plurality of postures.

2. The system of claim 1, wherein the calculation module is further configured to calculate the joint densities of probabilities $(P(x(n),y(n)))$ defined at values of the second variable and the first variable by computing the product of a density of probability $P_{x,i}$ of obtaining a value $(x(n))$ for the second variable and a density of probability $P_{y,i}$ of obtaining a value $(y(n))$ for the first variable, the density of probability $P_{x,i}$ of obtaining the value $(x(n))$ and the density of probability $P_{y,i}$ of obtaining the value $(y(n))$ being defined for each state i by the following expressions:

$$\begin{cases} P_{x,i}(x(n)) = \dfrac{1}{\sqrt{2\pi}\,\sigma_{x,i}} \cdot e^{-\dfrac{(x(n)-\mu_{x,i})^2}{2\sigma_{x,i}^2}} \\ p_{y,i}(y(n)) = \dfrac{1}{\sqrt{2^k}\,\sigma_{y,i}^k \Gamma\!\left(\dfrac{k}{2}\right)} y(n)^{k/2-1} e^{-\dfrac{y(n)}{2\sigma_{y,i}^2}} \end{cases}$$

where:
$x(n)$ is a one-dimensional value of the second variable at a sample index n;
$\mu_{x,i}$ is a vector of the same dimension as the second variable, which represents the state i of a hidden Markov model;
$\sigma_{x,i}$ is a square root of a variance of the second variable, which represents the state i of the hidden Markov model;
$y(n)$ is the value of the first variable at the sample index n;
k is the number of axes measured by the at least one motion sensor;
$\sigma_{y,i}$ is a quantity proportional to a temporal mean of the value $y(n)$, in the state i; and
$\Gamma$ is a gamma function that verifies $\Gamma(\frac{1}{2})=\sqrt{\pi}$, $\Gamma(1)=1$ and $\Gamma(n+1+\frac{1}{2})=n\Gamma(n+\frac{1}{2})$.

3. The system of claim 2, wherein said analysis module is configured for determining a posture of the person as a function of time, by using the hidden Markov model with four states including (1) a standing or seated posture, (2) a walking posture, (3) a leaning posture and (4) a recumbent posture.

4. The system of claim 3, wherein the system is further configured to determine the posture of the person according to the following:
    for the standing or seated posture, $\mu_{x,1} \in [0.7;1.3]$, $\sigma_{x,1} \in [0.05; 0.4]$, $\sigma_{y,1} \in [1\times10^{-3};5\times10^{-1}]$;
    for the walking posture, $\mu_{x,2} \in [0.7; 1.3]$, $\sigma_{x,2} \in [0.05; 0.4]$, $\sigma_{y,2} \in [1\times10^{-2};1]$;

for the leaning posture, $\mu_{x,3} \in [0.7; 1.3]$, $\sigma_{x,3} \in [0.05; 0.4]$, $\sigma_{y,3} \in [1\times10^{-3}; 5\times10^{-1}]$; and for the recumbent posture $\mu_{x,4} \in [-0.3; 0.3]$, $\sigma_{x,4} \in [0.05; 0.4]$, $\sigma_{y,4} \in [1\times10^{-3}; 5\times10^{-1}]$.

5. The system of claim 1, further comprising a display.

6. The system of claim 1, wherein the at least one motion sensor comprises an accelerometer, a magnetometer, a gyrometer or combinations thereof.

7. The system of claim 1, wherein the at least one motion sensor comprises a first accelerometer with a measurement axis and fixing element configured for fixing the first accelerometer to a torso of the person in such a way that the measurement axis coincides substantially with a vertical axis of a body when the person is upright.

8. The system of claim 7, wherein the at least one motion sensor comprises a second accelerometer with an axis of measurement and a fixing element configured for fixing the second accelerometer to a thigh of the person in such a way that the axis of measurement of the second accelerometer coincides with the vertical axis of the body when the person is upright.

9. The system of claim 8, wherein said analysis module is configured for determining a posture of the person as a function of time, by using a hidden Markov model, the hidden Markov model including at least two states selected from four states including (1) a standing posture, (2) a seated posture, (3) a recumbent posture, and (4) a walking posture.

10. The system as claimed in claim 9, wherein x(n) represents a vector comprising a pair of values of respective second variables of said two accelerometers, and y(n) represents a value of the first variable of said second accelerometer, at sample index n, and the system is further configured to compute the density of probability of obtaining the values x(n) according to the following expression:

$$P_{x,i}(x(n)) = \frac{1}{\sqrt{(2\pi)^2 |\Sigma_{x,i}|}} \cdot e^{-\frac{1}{2}(x(n)-\mu_{x,i})^T \Sigma_{x,ii}^{-1}(x(n)-\mu_{x,i})}$$

where:
$\Sigma_{x,i}$ is a two-dimensional diagonal matrix describing the covariance matrix of the value x(n) for a state i of the model;

$\Sigma_{x,i}^{-1}$ is an inverse of the two-dimensional diagonal matrix $\Sigma_{x,i}$; and $\mu_{x,i}$ represents a two-component column vector, representing the state i of the model.

11. The system of claim 10, wherein the system is further configured to determine the posture of the person according to the following:

for the standing posture, $\mu_{x,1}=[1\ 1]^T$, $$\Sigma_{x,1} = \begin{bmatrix} 0.03^2 & 0 \\ 0 & 0.03^2 \end{bmatrix},$$

and $\sigma_{y,1}=3e^{-2}$;

for the seated posture, $\mu_{x,2}=[1\ 0]^T$, $$\Sigma_{x,2} = \begin{bmatrix} 0.03^2 & 0 \\ 0 & 0.03^2 \end{bmatrix},$$

and $\sigma_{y,2}=3e^{-2}$;

for the recumbent posture, $\mu_{x,3}=[0\ 0]^T$, $$\Sigma_{x,4} = \begin{bmatrix} 0.03^2 & 0 \\ 0 & 0.03^2 \end{bmatrix},$$

and $\sigma_{y,3}=3e^{-2}$; and for the walking posture, $\mu_{x,4}=[1\ 1]^T$, $$\Sigma_{x,3} = \begin{bmatrix} 0.03^2 & 0 \\ 0 & 0.03^2 \end{bmatrix},$$

and $\sigma_{y,4}=1.2e^{-1}$.

12. A method for determining a posture of a person, comprising:

processing output signals of at least one motion sensor to produce first signals with frequencies above a first threshold selected for each axis of measurement, and second signals with frequencies below a second threshold lower than or equal to said first threshold, wherein the at least one motion sensor is configured to measure k measurement axes, k being equal to or greater than two;

calculating a density of probability of a first variable representative of said first signals and a density of probability of a second variable representative of said second signals, said first variable being modeled by a Chi-2 law with a degree of freedom equal to k, and said second variable being a one-dimensional variable representative of the second signals along the k axes of measurement and being modeled by a Gaussian law; and determining a posture of the person as a function of time, by using a hidden Markov model with N states corresponding respectively to N postures, the determination being carried out by utilizing:

joint densities of probabilities of said second and first variables, the joint densities of probabilities being defined for each posture of the N postures, and probabilities of transition between two successive postures of the N postures.

* * * * *